United States Patent
Pollock et al.

(10) Patent No.: US 10,247,707 B1
(45) Date of Patent: Apr. 2, 2019

(54) CEMENT COMPOSITIONS COMPRISING LOCALLY RESONANT ACOUSTIC METAMATERIALS

(71) Applicant: Oceanit Laboratories, Inc., Honolulu, HI (US)

(72) Inventors: Jacob Freas Pollock, Honolulu, HI (US); Chris Sullivan, Honolulu, HI (US); Vinod P. Veedu, Houston, TX (US); Robert Izuta, Honolulu, HI (US); Joanne Ebesu, Waipahu, HI (US)

(73) Assignee: OCEANIT LABORATORIES, INC., Honolulu, HI (US)

(*) Notice: Subject to any disclaimer, the term of this patent is extended or adjusted under 35 U.S.C. 154(b) by 111 days.

(21) Appl. No.: 15/048,352

(22) Filed: Feb. 19, 2016

Related U.S. Application Data

(63) Continuation of application No. 14/942,922, filed on Nov. 16, 2015, now abandoned.

(60) Provisional application No. 62/080,233, filed on Nov. 14, 2014.

(51) Int. Cl.
| | | |
|---|---|---|
| *G01N 29/12* | (2006.01) | |
| *C04B 20/10* | (2006.01) | |
| *C04B 7/02* | (2006.01) | |
| *G01N 33/38* | (2006.01) | |

(52) U.S. Cl.
CPC ............ *G01N 29/12* (2013.01); *C04B 7/02* (2013.01); *C04B 20/1007* (2013.01); *C04B 20/1037* (2013.01); *G01N 33/383* (2013.01)

(58) Field of Classification Search
CPC .. G01N 29/12; G01N 29/2437; G01N 29/341; G01N 29/343; G01N 29/2431; G01N 29/045; G01N 33/383; C04B 7/02; C04B 20/1037; C04B 20/1007;
(Continued)

(56) References Cited

U.S. PATENT DOCUMENTS

| | | | | |
|---|---|---|---|---|
| 8,191,401 | B2 * | 6/2012 | Daraio | G10K 15/00 73/12.11 |
| 8,327,709 | B2 * | 12/2012 | Daraio | G01N 29/2437 73/632 |
| 9,140,326 | B2 * | 9/2015 | Enoch | F42D 3/06 |

(Continued)

*Primary Examiner* — Helen C Kwok
(74) *Attorney, Agent, or Firm* — Symbus Law Group, LLC; Clifford D. Hyra

(57) ABSTRACT

A new cement formulation includes a base cement slurry and an admixture of acoustic metamaterial particles, the acoustic metamaterial particles each having a dense inner core and compliant surrounding matrix. The cement formulation exhibits a substantial increase in transmission loss over the base cement slurry at a first frequency, and does not exhibit a substantial increase in transmission loss over the base cement slurry at a second frequency. A new cement interrogation technique involves transmitting acoustic energy at and near the band-gap frequency of an acoustic metamaterial, detecting an acoustic response and analyzing it for band-gap performance involving substantially elevated transmission loss at or near a given first frequency that rapidly falls off at nearby frequencies, determining that the cement formulation is present in regions exhibiting band-gap performance, and determining that the cement formulation is not present and/or has been compromised in regions not exhibiting band-gap performance.

20 Claims, 12 Drawing Sheets

(58) Field of Classification Search
CPC .. G10K 11/172; G10K 11/175; G01K 11/165; G01K 11/16
See application file for complete search history.

(56) References Cited

U.S. PATENT DOCUMENTS

| | | | |
|---|---|---|---|
| 9,581,715 B1* | 2/2017 | Swett | G01V 1/44 |
| 2011/0085232 A1* | 4/2011 | Werner | B82Y 20/00 |
| | | | 359/350 |
| 2014/0239164 A1* | 8/2014 | Rothrock | G01N 21/534 |
| | | | 250/227.11 |
| 2014/0305049 A1* | 10/2014 | Kim | E04H 9/02 |
| | | | 52/167.2 |
| 2014/0318886 A1* | 10/2014 | Yano | G10K 11/165 |
| | | | 181/207 |
| 2014/0371353 A1* | 12/2014 | Mitchell | C04B 28/02 |
| | | | 524/5 |
| 2016/0027427 A1* | 1/2016 | Yang | G10K 11/172 |
| | | | 181/286 |
| 2016/0376192 A1* | 12/2016 | Mitchell | C04B 28/02 |
| | | | 524/439 |
| 2017/0365365 A1* | 12/2017 | White | G21F 1/042 |
| 2018/0023599 A1* | 1/2018 | Hussein | F15D 1/006 |

* cited by examiner

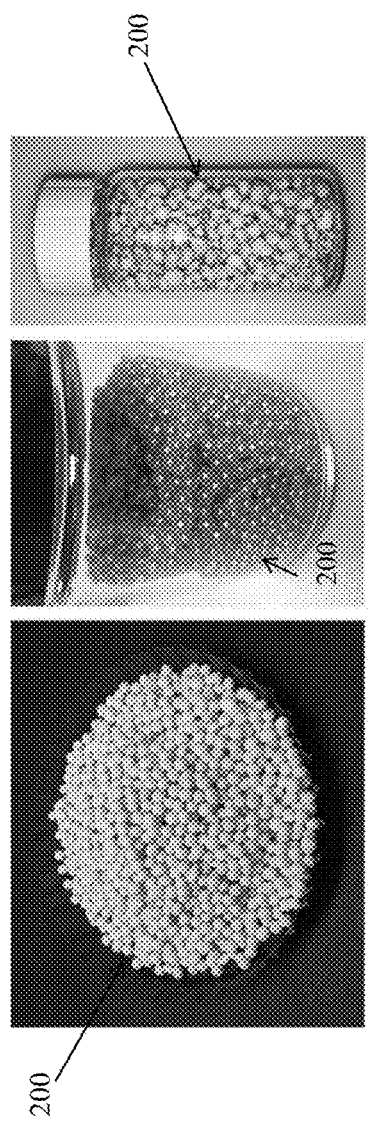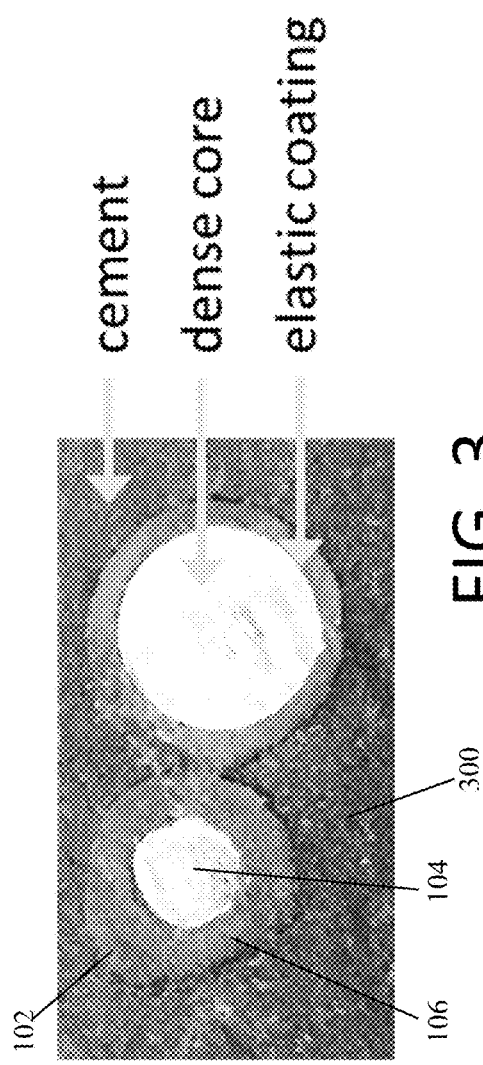

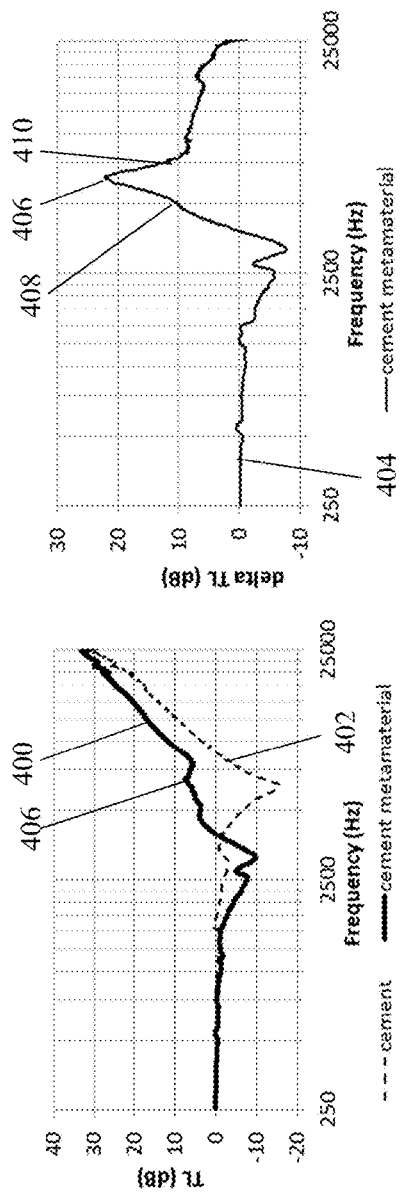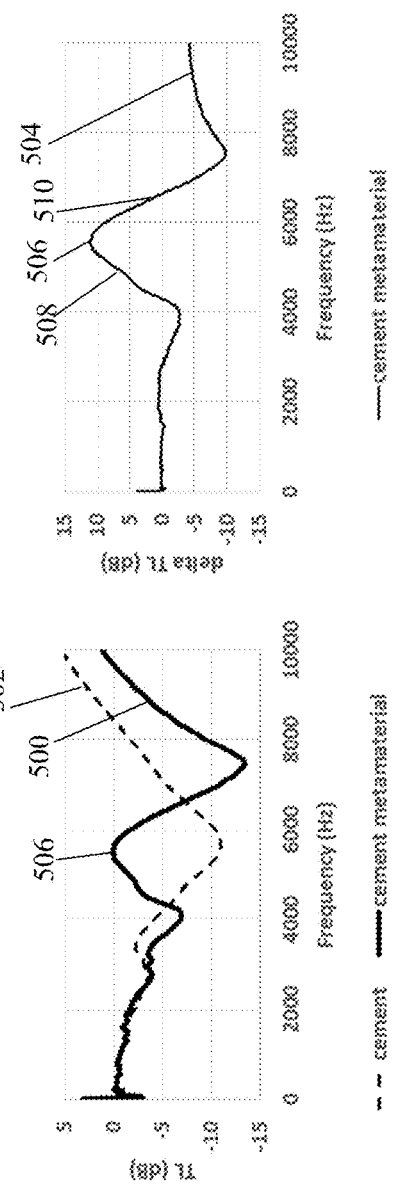
FIG. 4B
FIG. 5B
FIG. 4A
FIG. 5A

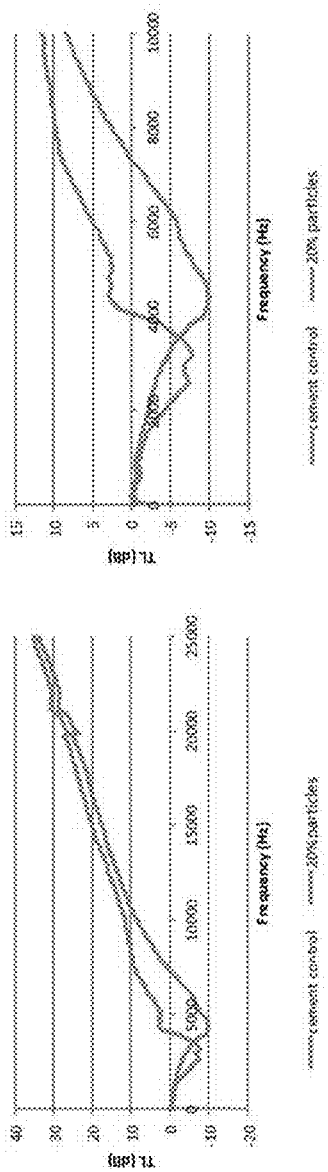
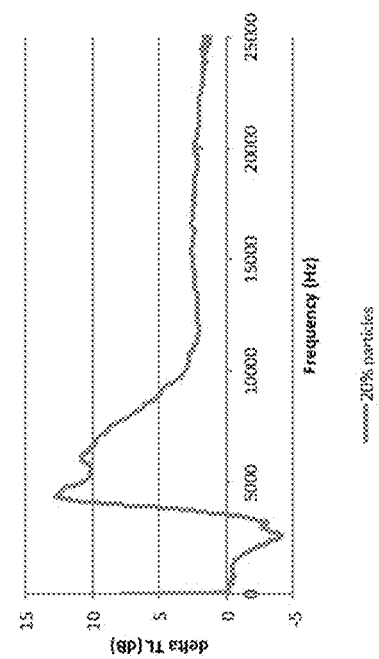
FIG. 11A
FIG. 11B
FIG. 11C

CEMENT COMPOSITIONS COMPRISING LOCALLY RESONANT ACOUSTIC METAMATERIALS

This application is a continuation of U.S. application Ser. No. 14/942,922 filed Nov. 16, 2015, which claims priority to Provisional Application No. 62/080,233, filed Nov. 14, 2014, which are hereby incorporated by reference in their entirety.

FIELD OF THE INVENTION

The application relates generally to cement and particularly to cement evaluation.

BACKGROUND

Hydraulic cement has a wide variety of applications in which it provides positioning and structural integrity. The ability to detect the location and environmental condition of cement can be used to detect or prevent failure and improve the design and performance of structures made out of it.

Cementing is a crucial step in drilling safely for oil and natural gas. However, it can be prone to frequent failures which compromise well integrity, productivity, and safety. Also this important barrier provides isolation of production phases within the well and separation of the well and the aquifer. Cement sheath integrity is a key factor controlling the life of the well. Risks to well integrity must be addressed and mitigated up-front.

Acoustic interrogation techniques that can be applied to cement and geophysical measurement and monitoring range in frequency from sub-sonic (or seismic) to ultra-sonic. They typically involve use of a sound source and a series of detectors that measure acoustic reflections. The sound wavelengths largely determine the range and resolution of measurements. Advanced signal processing can be applied to the response to allow for improved acoustic mapping. Fiber optic cable can be used for distributed acoustic sensing, providing additional opportunities for acoustic analysis. In the case of cemented oil and gas wells, aside from acoustic stimulation from within the wellbore fluid, the casing itself can be stimulated by a mechanical or electromagnetic-acoustic means as a sound source for acoustic interrogation. These methods can also be used to create acoustic relays to convey information along the wellbore.

Conventional techniques to inspect the integrity of cementing behind multiple casing strings are inaccurate, insufficient, and not reliable. Traditional sonic cement bond logs provide some information regarding the bond between the cement and the casing, but provide little information about the cement itself and are often difficult to interpret. Existing evaluation techniques have been used for over thirty years and provide little accuracy. One major problem is that lightweight or contaminated cement has similar acoustic impedance as surrounding fluids, making it difficult to distinguish. Additional acoustic methods for well cement and formation evaluation include cross-well tomography, full waveform imaging, pulse-echo techniques, and flexural wave propagation measurements.

Sound sources for seismic measurements include sparkers, boomers, and chirp transducers and cover a range of lower frequencies. These sources provide good resolution to about 30 feet and lower resolutions up to 100's of feet. Traditional downhole sonic logging tools have a depth of penetration of about one source wavelength, typically 1 to 5 feet. Borehole acoustic reflection surveys use seismic processing methods with a downhole tool to map fractures up to 15 feet away from the wellbore. Cross-well seismic imaging provides similar ranges and resolutions as surface seismic, but measure across the formation instead of down into it. Improved materials for and methods of cement evaluation are needed to improve the range and resolution of such measurements.

Needs exist for improved cement evaluation technologies and approaches to improve the effectiveness of existing technologies to assess cement integrity.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description.

In certain embodiments, the disclosed embodiments may include one or more of the features described herein.

The ability to reliably detect cement location and integrity will greatly enhance the design and use of structures made out of it. As an example, in the upstream oil and gas industry there is a shift in philosophy from periodic to continuous optimization as digital oilfield technologies are integrated into "smart fields". Much more information is collected, intelligently analyzed, and used to make well planning and management decisions. Real-time monitoring and analysis on a zone-by-zone basis allows adjustment of production rates from different reservoir areas as required. A smart cement that can be effectively interrogated for location and condition using acoustic techniques will greatly enhance the smartness of the field. Remote sensing of cement presence and environmental condition complements and provides redundancy for other current and proposed monitoring systems, such as distributed sensing via fiber optic cable.

A new cement formulation includes a base cement slurry and an admixture of acoustic metamaterial particles, the acoustic metamaterial particles each having a dense inner core and compliant surrounding matrix. The cement formulation exhibits a substantial increase in transmission loss over the base cement slurry at a first frequency, and does not exhibit a substantial increase in transmission loss over the base cement slurry at a second frequency. A substantial increase in transmission loss may be a given preset number of decibels, such as at least 5 dB or at least 10 dB. The second frequency may be within 5 kHz of the first frequency. There may be multiple such first frequencies and/or second frequencies. Transmission loss may be measured for these purposes using a solid vibration analysis. The amount of transmission loss may vary in practical applications depending on the measurement geometry and environment. Corresponding non-cement formulations (such as plastics) are the same except that they substitute a different matrix (such as a base plastic material) in place of the base cement slurry.

A new cement formulation may include an admixture of acoustic metamaterial particles, the acoustic metamaterial particles each having a dense inner core and compliant surrounding matrix, the acoustic metamaterial particles exhibiting acoustic reflection at a local resonant frequency and acoustic transparency at other frequencies. A frequency where acoustic reflection is exhibited and away from which acoustic transparency is exhibited is referred to as a band-gap frequency, since band-gap behavior is exhibited at the frequency. As this band-gap behavior is exhibited at the local resonance frequency of the acoustic metamaterial, local resonance frequency is typically the same as observed band-gap frequency. The dense inner core is more dense than the matrix material (cement), for example 3 to 15 g/cc. The dense inner core in embodiments is also stiff, with a Young's modulus greater than 5 GPa. The compliant surrounding matrix is more compliant than the matrix material (cement) or the dense core, in embodiments having a Young's modulus of less than 10 GPa. Acoustic transparency and reflection as used herein are relative, as such materials will generally exhibit some attenuation at all frequencies. Acoustic reflection may for example be defined as a reflection coefficient of greater than 0.5, and acoustic transparency as a reflection coefficient of less than 0.5. The acoustic metamaterial particles may be configured to exhibit a given preselected difference in coefficient of reflection between two given preselected frequencies. The elastic coating can be low density to produce a layered particle with an overall density that matches that of the cement slurry (e.g. within 25%). This can be accomplished with a foam elastomer precursor formulation using, for example, air or air-filled microballoons. A prepolymer or polymer solution for the coating may be used that is gas entrained or that produces gas during polymerization, such as with a polyurethane elastomer. Microballoons may be added to a polymer solution to reduce its density prior to depositing it as a coating. Each of the acoustic metamaterial particles may also have a rigid outer shell or an outer coating or surface modification to improve bond with cement matrix.

A new cement interrogation technique may involve transmitting acoustic energy at and near the band-gap frequency of an acoustic metamaterial in an area where a cement formulation comprising the acoustic metamaterial was meant to be placed, detecting an acoustic response, analyzing the acoustic response for band-gap performance comprising near-total reflectance at or near the band-gap frequency that rapidly falls off to transparency at nearby frequencies, determining that the cement formulation is present in regions exhibiting band-gap performance, and determining that the cement formulation is not present and/or has been compromised in regions not exhibiting band-gap performance. In some embodiments, the near-total reflectance is exhibited by the material over a long stretch of frequencies, such as 10s of KHz, before dropping off to transparency. In other embodiments, presence of the cement formulation may be determined by acoustic reflectance that differs substantially (e.g. a given predetermined level) from known background materials at a given frequency such as the band-gap frequency of the acoustic metamaterial. Depending on the type and amount of acoustic metamaterial incorporated into the cement formulation, the cement formulation may not exhibit a classic band-gap response, but rather exhibit elevated reflectance in a given range of frequencies, for example low frequencies under 10 KHz. A common acoustic response for the cement formulations is an elevated reflectance and transmission loss within a given band of frequencies, accompanied by no elevated reflectance, and even reduced reflectance, at nearby frequencies. For example, the acoustic response may involve a lower than normal reflectance and transmission loss below 5 kHz, a band of substantially (e.g. 5 dB, 10 dB, up to 30 dB or more) elevated transmission loss and reflectance in a band of frequencies such as 5-10 kHz, and continued elevated transmission loss where the delta TL gradually decreases over 10s of kHz. A local resonance frequency and/or response shape of the interrogated material may be determined based on the acoustic response, the difference between the acoustic reflection at the local resonance frequency and surrounding frequencies may be determined, and stress and/or curing progression in the interrogated material may be determined using the difference and/or response shape.

Improved contrast provides improved feature discernment using existing acoustic interrogation methods. The unique spectral response allows new forms of acoustic interrogation, such as for cement imaging.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art.

FIGS. 2A-C show photographs of composite layered particles for incorporation in the metamaterial cement.

FIG. 3 is a cross section of a layered particle embedded in cement showing the cement matrix, dense core, and elastic coating.

FIGS. 4A-B are plots of transmission loss versus frequency (FIG. 4A) of the vibration analysis response of a composite cement metamaterial sample along with the difference in transmission loss between the metamaterial cement and base cement (FIG. 4B).

FIGS. 5A-B are plots of transmission loss versus frequency (FIG. 5A) of the vibration analysis response of a composite cement metamaterial sample with neutrally buoyant layered particles along with the difference in transmission loss between the metamaterial cement and base cement (FIG. 5B).

FIGS. 11A-C are plots of TL versus frequency for ordinary cement versus cement modified with the addition of 20% acoustic metamaterial particles by weight, and of delta TL versus frequency, respectively.

DETAILED DESCRIPTION

Figures 1A, 1B:
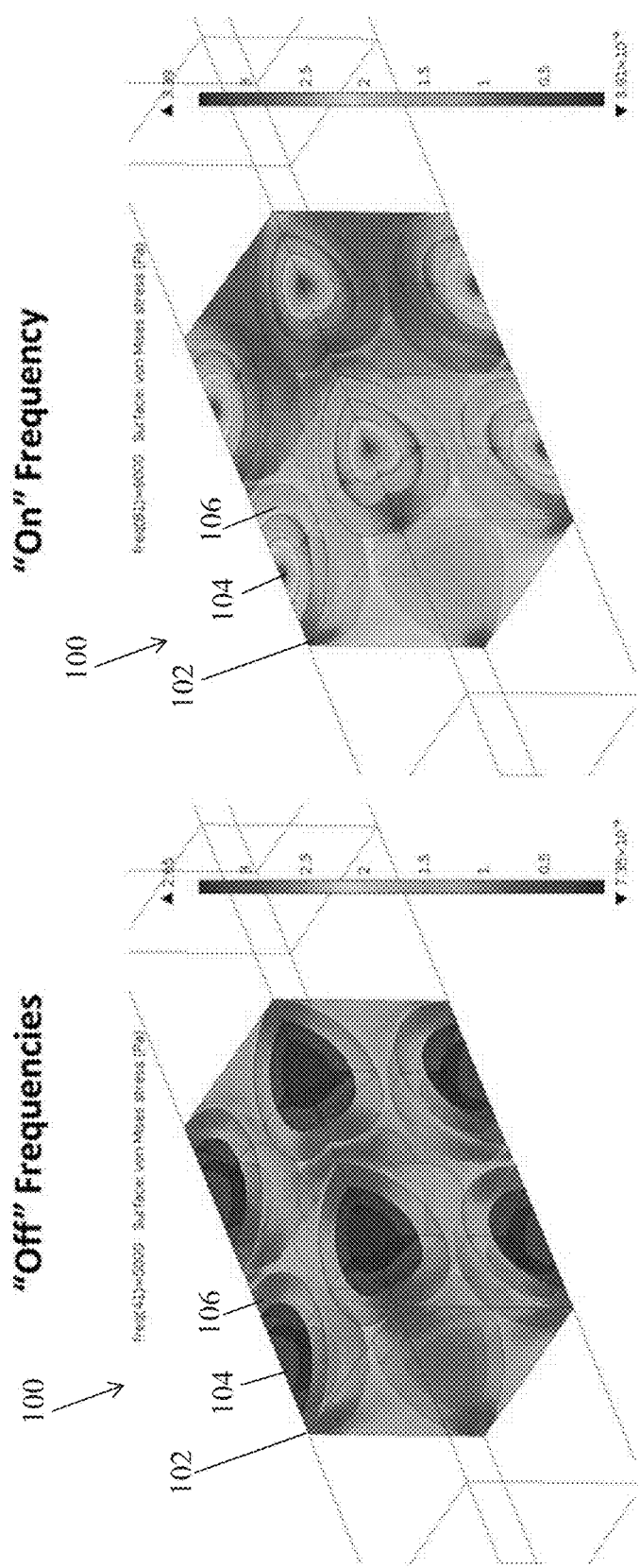
FIGS. 1A-B are maps of the Von Mises stress in the cement metamaterial composite structure at frequencies away from the acoustic band gap (FIG. 1A) and at the acoustic band gap (FIG. 1B).

Cement compositions comprising locally resonant acoustic metamaterials will now be disclosed in terms of various exemplary embodiments. This specification discloses one or more embodiments that incorporate features of the invention. The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

In the several figures, like reference numerals may be used for like elements having like functions even in different drawings. The figures are not to scale. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items. As used herein, the singular forms "a", "an" and "the" are intended to include the plural forms as well, unless the context clearly indicates otherwise.

A new cement formulation may be used for downhole monitoring of cement placement and integrity. Its unique acoustic properties allow it to be detected remotely for determining the presence and integrity of cement, such as around casing pipe, and generally in underwater or other liquid environments and/or embedded within solid structures. Furthermore, the environmental condition of the cement, such as stress induced by compaction or sustained casing pressure, can be interrogated using acoustic techniques. These useful characteristics are imparted through addition of filler particles that act as an acoustic metamaterial.

Metamaterials are characterized by their ability to alter interactions with wavelengths orders of magnitude larger than the feature size of the material. Acoustic metamaterials may be engineered in known ways to influence sound transmission at specific frequencies and act as band gap filters. These materials are relatively acoustically transparent (e.g. reflectance coefficient <0.5) at most frequencies but reflect much or all sound (e.g. reflectance coefficient >0.5) at particular frequencies. This effect is due to local resonance within the material's substructures.

The structures of the filler particles are based on locally resonant metamaterial substructures developed as acoustic band gap filters. The particles have a layered structure with a dense core and compliant coating. Such particle structures are described in related U.S. application Ser. No. 61/975,389, filed Apr. 4, 2014, by the same Applicant, which is hereby incorporated by reference in its entirety. Material selection for elements of the particles is based largely on density and mechanical properties needed for a particular application. They may also be selected for compatibility with cement and performance at downhole temperatures and pressures, which may range up to 500° F. and into the tens of thousands, or higher, of PSI. Materials may include steel, lead, tungsten, or other metals or dense minerals for the dense core and silicone or polyurethane for the elastic coating. Optionally, the particles may have a stiff outer shell, such as epoxy or metal. They may also have an outer coating or surface treatment that improves their bond to the cement matrix, for example where a hydrophobic polymer coating is used with hydrophilic cement. In embodiments, the size of the particles may range from about 50 micrometers to about 2 cm and cement formulations may include 0.1-40% of the particles by weight. 40% metamaterial particles by weight may represent a completely packed admixture. FIGS. 4A-B and 5A-B show characteristics of concrete formulations containing 10-20% metamaterials. A greater proportion of acoustic metamaterial generally brings the acoustic response of the cement metamaterial closer to that of the metamaterial itself. A wide variety of particle sizes, layer thicknesses, materials, and cement formulations may be used. These attributes may be controlled to obtain desired acoustic responses (i.e. band gap frequency, response shape) under desired conditions while maintaining the strength and other material properties of the cement, using known experimental techniques. For example, increasing the total radius of the particle, or increasing the density of the core, may decrease the resonance frequency. Also, changing the matrix or the core size alter the frequency response.

The layered particles may be produced by a variety of known coating and composite formulation methods. For example, they may be produced using pan coating or fluidized bed. Alternatively, the dense core material and the elastic material may be mixed together and pelletized to produce particles. The mixing may occur before the elastic material has substantially set (while the elastic material is still a liquid and can flow) as a one component or two component system. A key element is that the dense material is at least partially suspended by the elastic material within the particles.

The novel cement compositions are engineered with specific acoustic band gap filter properties based on the geometry and mechanical properties of the composite filler material. The mode of interrogation of the cement determines the range and resolution of the measurements. Options for remote sensing range from surface seismic to downhole acoustic logging techniques. An impulse or continuous sound source may be used to stimulate the material. A key feature of the cement is its frequency-dependent response that allows its specific detection by comparing acoustic results at two different frequencies. Other materials do not exhibit acoustic transparency at one frequency and nearly total reflection at a nearby frequency, thus this response is a highly accurate indicator of the presence of the cement. Environmental conditions such as background well and formation properties (in oil and gas applications) can be measured at frequencies at which the cement compositions are acoustically transparent, with cement composition location and integrity detected at an adjacent frequency at which it is acoustically opaque.

Another feature of the novel cement is the ability to alter the frequency response based on curing and its environmental condition. Curing changes the local mechanical environment of the metamaterial particles, resulting in a development of acoustic characteristics, such as evolving acoustic impedance, corresponding to stiffness and compressive strength as the cement slurry sets from a liquid into a solid. Typically, this will gradually shift the local resonant frequency at which the material exhibits near-total reflection (band gap frequency). Changes in the local resonant frequency over time can therefore be used to estimate the extent of curing the cement has experienced. In another example, stress on the metamaterial structure shifts the frequencies at which the band gap occurs, for example due to compression of filler particle elastic component which changes its mechanical properties, allowing the local formation or casing pressure to be gauged. Higher stress may result in a shift to a higher band gap frequency. If the material is damaged and liquids (e.g. water or oil) infiltrate, the frequency response may no longer occur in that region, as the liquid causes an acoustic short-circuit. As cement typically solidifies in about eight hours, and then continues curing for about a month, changes occurring after this period can be attributed to stress on the material. Regular interrogation during the curing process allows the progression in acoustic response characteristics during curing to be determined for a given cement composition.

The new cement compositions have very high acoustic impedance at the band gap frequency, in embodiments 8 Mrayl or more, with lower values being typical of light vs. neat compositions. Such compositions which have been contaminated exhibit much lower acoustic impedance, around 4 Mrayl. Thus the compositions have great contrast between contaminated and non-contaminated portions, allowing for easy identification of contamination. In contrast, ordinary cement exhibits acoustic impedance between 2 Mrayl for light cement and 8 Mrayl for neat, a range that overlaps entirely with the acoustic impedance of ordinary cement with varying levels of contamination (typically the greater the contamination, the lower the acoustic impedance), as well as with liquids. At a measurement of 2 Mrayl, the observed acoustic impedance could indicate the presence of liquid fossil fuels, light and uncontaminated ordinary cement, or very contaminated neat cement, for example.

Together, these abilities provide a large amount of new information regarding cement location and condition. To locate and interrogate the novel cement compositions, acoustic energy at and near the band-gap frequency may be transmitted into the area where the cement was meant to be placed. If material is detected that exhibits near-total reflectance at the band-gap frequency that rapidly falls off to transparency at nearby frequencies, that material is confirmed as the cement. If the band gap frequency and/or response shape differs from the expected, but still exhibits the general pattern of a near-total reflectance in a narrow frequency and relative transparence outside of that frequency, the material is confirmed as such cement that has cured and/or is under stress, and the type and magnitude of the changes may be used to determine the extent of curing and/or magnitude and direction of the stress. If no such response is exhibited, a conclusion is drawn that the novel cement either is not present at the area, or has been compromised, allowing liquid infiltration.

FIGS. 1A-B are maps of the Von Mises stress in the cement metamaterial composite structure 100 at frequencies away from the acoustic band gap (FIG. 1A) and at the acoustic band gap (FIG. 1B). Metameterial particles 102 in the structure 100 have a dense core 104 and elastic coating 106. At the off (non-resonant) frequency (FIG. 1A), the material is nearly transparent, exhibiting little von Mises stress, while at the on (resonant) frequency (FIG. 1B) the material exhibits substantially greater von Mises stress at the composite interfaces.

FIGS. 2A-C show photographs of composite layered particles 200 for incorporation in the metamaterial cement.

FIG. 3 is a cross section of layered particles 102 embedded in cement 300 showing the cement matrix 300, dense core 104, and elastic coating 106.

FIGS. 4A-B are plots of transmission loss versus frequency (FIG. 4A) of the vibration analysis response of a composite cement metamaterial cylindrical plug sample 400 vs. base cement 402 along with the difference in transmission loss between the metamaterial cement and base cement 404 (FIG. 4B). This data was produced with a vibration analysis setup including a vibration measurement exciter connected to a signal generator and amplifier and fitted with one accelerometer upon which the composite cement metamaterial sample was placed with wax at the interface. Another accelerometer was affixed with wax to the top of the composite sample. A linear frequency sweep was created by the signal generator between 100 Hz and 40,000 Hz. The transfer function was calculated for the top and bottom accelerometers and corrected for the base frequency response when the transducers were connected directly and stimulated. The transmission loss was thus calculated as a function of frequency for the cement control and the cement metamaterial composite and compared.

These graphs and particularly the delta TL in FIG. 4B between the cement metamaterial and ordinary cement show the influence of the metamaterial on the acoustic response characteristics of the cement composition. Transmission loss includes loss due to reflectance and due to absorption, and therefore reflectance cannot be determined directly from these results. However, the reflectance of the metamaterial at certain frequencies drives the changes in transmission loss for the cement metamaterial as a whole. Frequencies of high reflectance are indicated by a positive peak in transmission loss (TL). The delta TL implies a metamaterial acoustic band gap of approximately 6,000 Hz 406, where delta TL is about 22 dB, or a signal power loss of over 99%. At nearby frequencies of 5,000 Hz 408 and 7,500 Hz 410, delta TL is about 10 dB, or a signal power loss of only 90%.

With this particular cement metamaterial composition, classic band-gap behavior of the material is not clearly observable in the graph of TL. However, even a composition that does not exhibit such behavior may still be very useful for cement evaluation in a variety of applications. As long as the cement metamaterial exhibits a substantially different acoustic response in some frequency range than the surrounding environment (e.g. the ground, water, other building materials etc), its presence can be readily identified and changes in its acoustic response can be identified and interpreted. In FIG. 4A, it can be seen that the cement metamaterial exhibits a high TL at very low frequencies (e.g. 5-10 kHz) which is very different from ordinary cement and many other materials. Thus such a material may be readily identified by acoustic interrogation in that frequency range, and compromised cement metamaterial may be identified where the material has lost this unique acoustic response (e.g. due to liquid infiltration), and changes to this acoustic response may be interpreted as curing or stress depending on the circumstances.

FIGS. 5A-B are plots of transmission loss versus frequency (FIG. 5A) of the vibration analysis response of a composite cement metamaterial sample with neutrally buoyant layered particles 500 vs. base cement 502 along with the difference in transmission loss between the metamaterial cement and base cement 504 (FIG. 5B). This data was produced with a vibration analysis setup similar to that of FIGS. 4A-B. At the metamaterial acoustic band gap of approximately 5,700 Hz 506, delta TL is about 11 dB, or a signal power loss of about 95%. At a nearby frequency of 5,000 Hz 508, delta TL is about 6 dB, a signal power loss of about 75%, and at 6,500 Hz 510 the delta TL is about 1.5 dB, or a signal power loss of about 30%. With this cement metamaterial composition, band-gap behavior of the material is observed in the graph of TL, with a peak TL of 0 dB at around 5,700 Hz and dropping to −5 dB at around 4,200 Hz and 6,200 Hz (negative readings being an effect of the testing method).

Figure 6A:
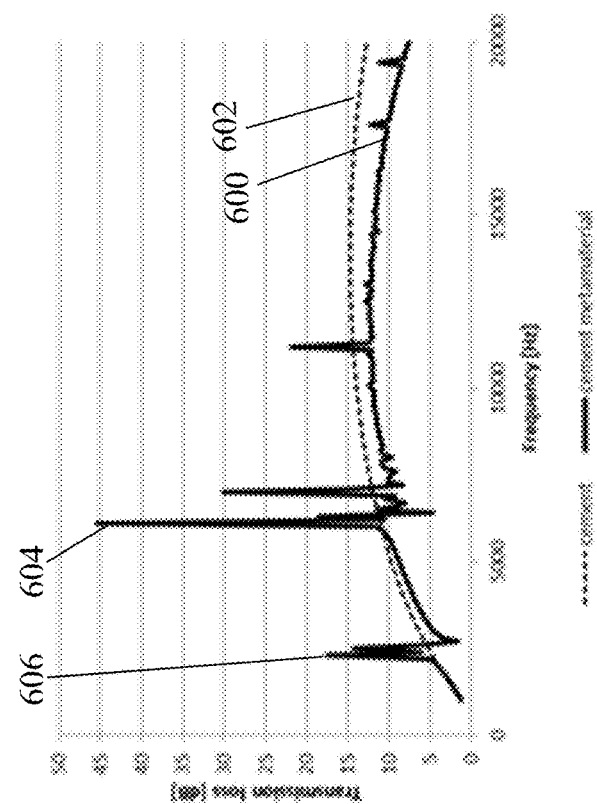
FIGS. 6A-B are plots of transmission loss versus frequency (FIG. 6A) of the vibration analysis response of a composite cement metamaterial sample and of reflection coefficient versus frequency (FIG. 6B) for the composite cement metamaterial.
Figure 6B:
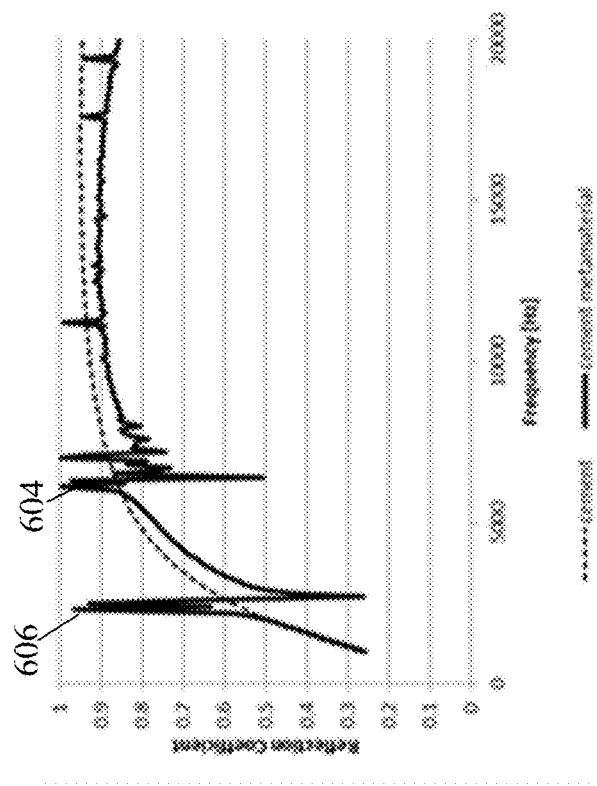

FIGS. 6A-B are plots of transmission loss versus frequency (FIG. 6A) of the vibration analysis response of a composite cement metamaterial sample 600 vs. base cement 602 and of reflection coefficient versus frequency (FIG. 6B) for the composite cement metamaterial vs. base cement. The data in FIG. 6A was produced with a vibration analysis setup similar to that used with FIGS. 4A-B. The data in FIG. 6B is simulated. The cement metamaterial exhibits strong acoustic band gap performance at approximately 6,000 Hz 604, where measured TL exceeds 45 dB, dropping away to less than 10 dB within 500 Hz higher and lower frequency, and simulated reflection coefficient approaches 1. Similar band-gap behavior is observed at approximately 2200 Hz 606, where measured TL exceeds 15 dB, dropping away to less than 5 dB within 500 Hz higher and lower frequency, and simulated reflection coefficient exceeds 0.95, exceeding that of ordinary cement by about 0.4. This example has a high metamaterial proportion/particle loading.

Figure 7:
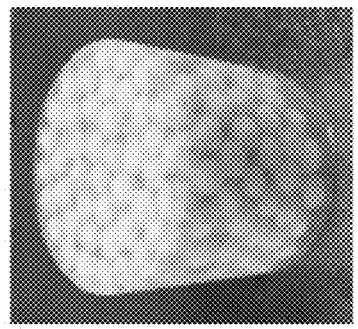
FIG. 7 shows acoustic metamaterial particles in polyurethane, according to an embodiment of the present invention.

FIG. 7 shows acoustic metamaterial particles in polyurethane, according to an embodiment of the present invention.

Figure 8B:
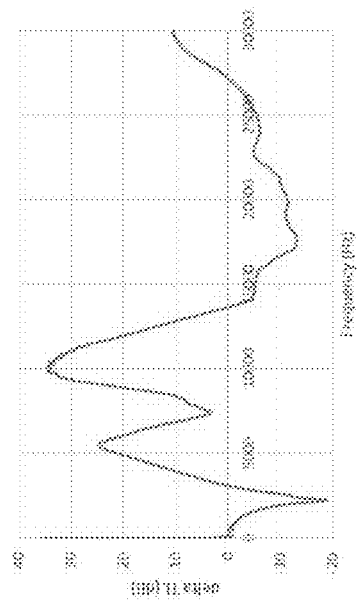
FIGS. 8A-B are plots of TL versus frequency for ordinary polyurethane versus polyurethane modified with acoustic metamaterial particles as shown in FIG. 7, and of delta TL versus frequency, respectively.
Figure 8A:
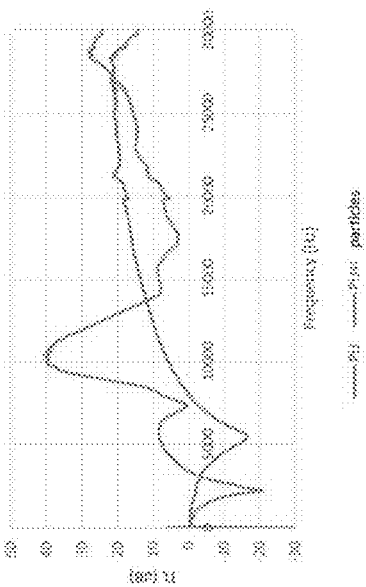

FIGS. 8A-B are plots of TL versus frequency for ordinary polyurethane versus polyurethane modified with acoustic metamaterial particles as shown in FIG. 7, and of delta TL versus frequency, respectively. The bandgap behavior of the modified polyurethane around 10 KHz is very noticeable. There is also a very substantial change in TL around 5 kHz.

Figure 9A:
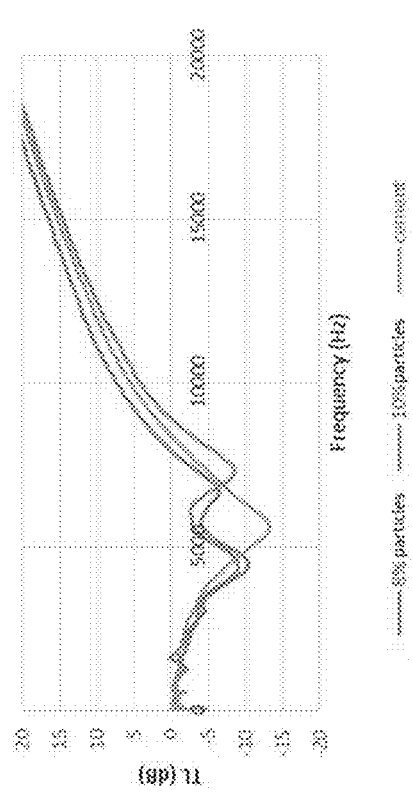
FIGS. 9A-B are plots of TL versus frequency for ordinary cement versus cement modified with the addition of 8% or 10% acoustic metamaterial particles by weight, and of delta TL versus frequency, respectively.
Figure 9B:
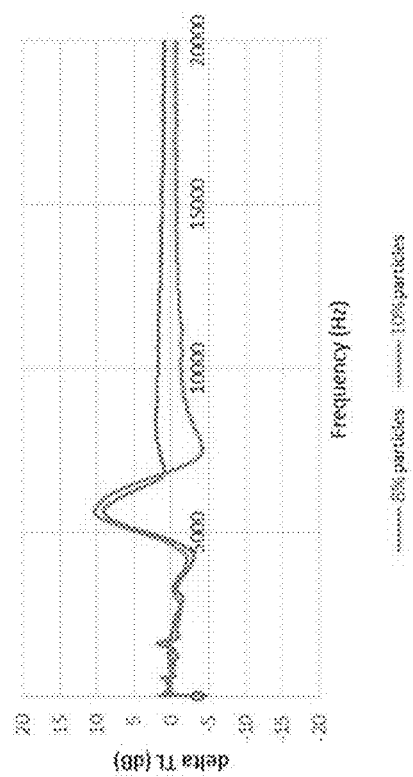

FIGS. 9A-B are plots of TL versus frequency for ordinary cement versus cement modified with the addition of 8% or 10% acoustic metamaterial particles by weight, and of delta TL versus frequency, respectively. The increase from 8% to 10% acoustic metamaterial particles is observed to strengthen the band-gap behavior of the modified cement and increase the difference in TL versus unmodified cement.

The metamaterial particles in the metamaterial modified materials of FIGS. 7-9 are similar to those of Example 3 (infra), with the dense inner cores of the particles being steel balls of 3/32" diameter.

Figure 10C:
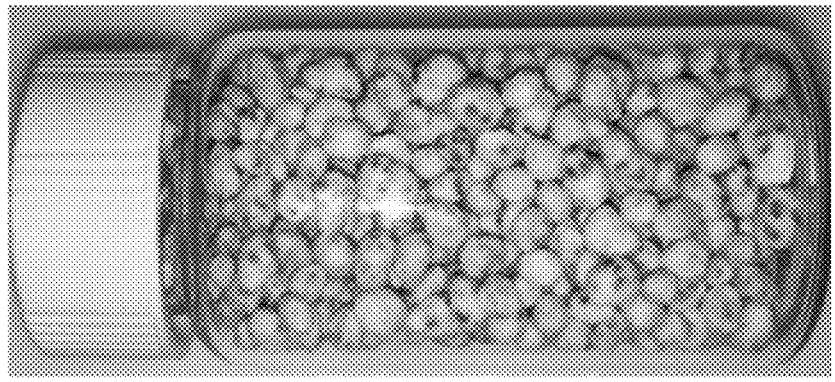
FIGS. 10A-C show acoustic metamaterial-coated tungsten particles of 1.7 mm, 2.4 mm, and 5.1 mm diameter, respectively, and having a density of 1.9-3.2 g/cc (FIG. 10A) and 2.2 g/cc (FIG. 10B), in embodiments of the present invention.
Figure 10B:
Figure 10A:

FIGS. 10A-C show acoustic metamaterial-coated tungsten particles of 1.7 mm, 2.4 mm, and 5.1 mm diameter, respectively, and having a density of 1.9-3.2 g/cc (FIG. 10A) and 2.2 g/cc (FIG. 10B), in embodiments of the present invention.

FIGS. 11A-C are plots of TL versus frequency for ordinary cement versus cement modified with the addition of 20% acoustic metamaterial particles by weight, and of delta TL versus frequency, respectively. Band-gap behavior is not pronounced, but a substantially elevated TL is noted in the 5-10 kHz frequency range with a decreased TL around 3 kHz.

Figure 12A:
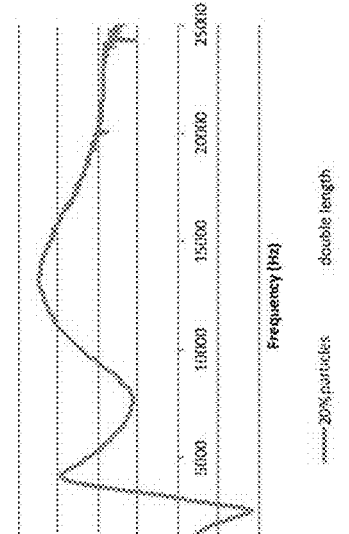
FIGS. 12A-B are plots of TL versus frequency for an ordinary cement sample versus a double-length sample of cement modified with the addition of 20% acoustic metamaterial particles by weight, and of delta TL versus frequency, respectively.
Figure 12B:
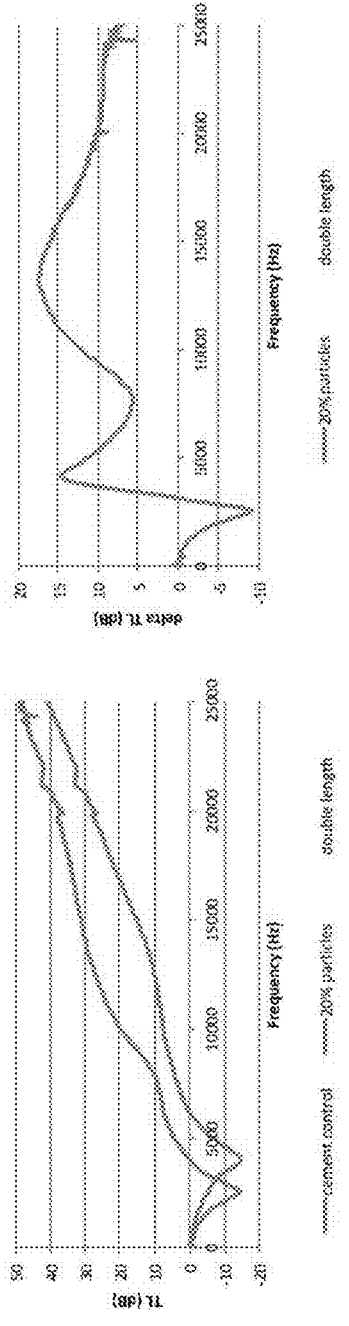

FIGS. 12A-B are plots of TL versus frequency for ordinary cement samples versus double-length samples of cement modified with the addition of 20% acoustic metamaterial particles by weight, and of delta TL versus frequency, respectively. Again, band-gap behavior is not pronounced but TL is substantially elevated around 5 kHz and 10-15 kHz and decreased around 3 kHz. The increased proportion of acoustic metamaterial particles has increased the delta TL magnitude while retaining the relevant frequencies, although an additional frequency range of elevated TL has been added.

Figure 13A:
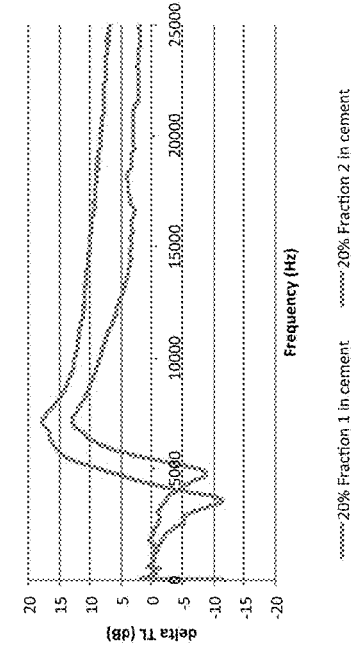
FIGS. 13A-B are plots of TL versus frequency for ordinary cement versus cement modified with the addition of 20% acoustic metamaterial particle fractions by weight, and of delta TL versus frequency, respectively.
Figure 13B:
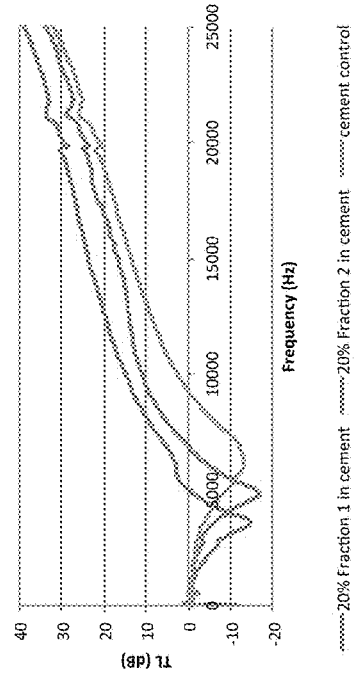

FIGS. 13A-B are plots of TL versus frequency for ordinary cement versus cement modified with the addition of 20% acoustic metamaterial particle fractions by weight, and of delta TL versus frequency, respectively. Fraction 2 exhibits larger magnitude delta TL, with both fractions exhibiting substantially lowered TL before 5 kHz and substantially elevated TL just after.

Figures 14A, 14B:
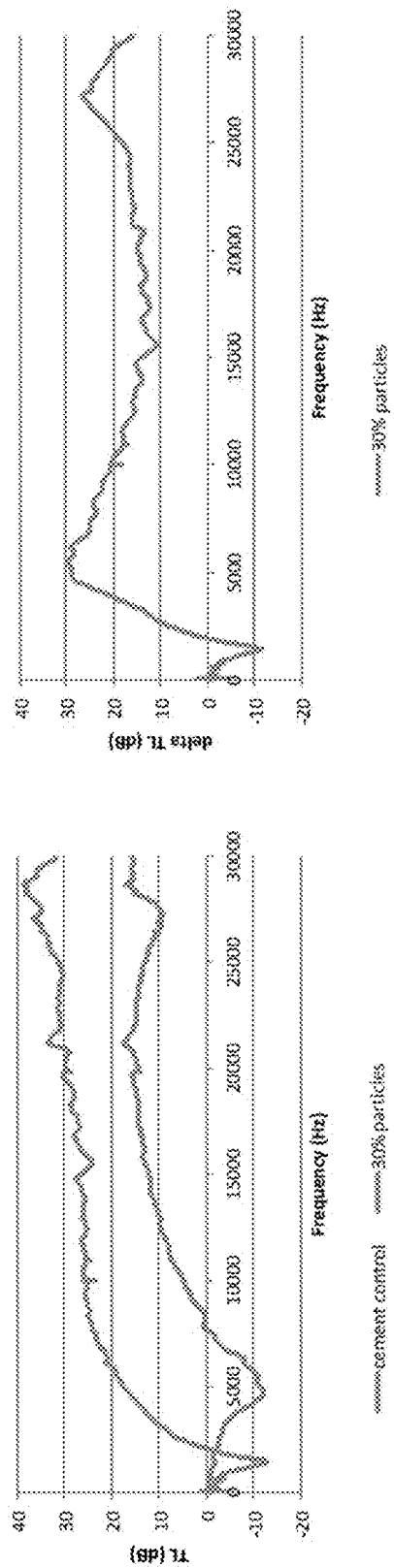
FIGS. 14A-B are plots of TL versus frequency for ordinary cement versus cement modified with the addition of 30% acoustic metamaterial particles by weight, and of delta TL versus frequency, respectively.

FIGS. 14A-B are plots of TL versus frequency for ordinary cement versus cement modified with the addition of 30% acoustic metamaterial particles by weight, and of delta TL versus frequency, respectively. At this elevated proportion of acoustic metamaterial particles, TL is very substantially elevated around 5 kHz, by about 30 dB, while around 2 kHz TL is lowered by 10 dB versus base cement. This is a very dramatic change in acoustic response.

The metamaterial particles in the metamaterial modified cements of FIGS. 11-14 are those described in Example 3 (infra), and the metamaterial modified cement of FIGS. 11-13 are samples of the cement composite described in Example 4 (infra).

Figure 15:
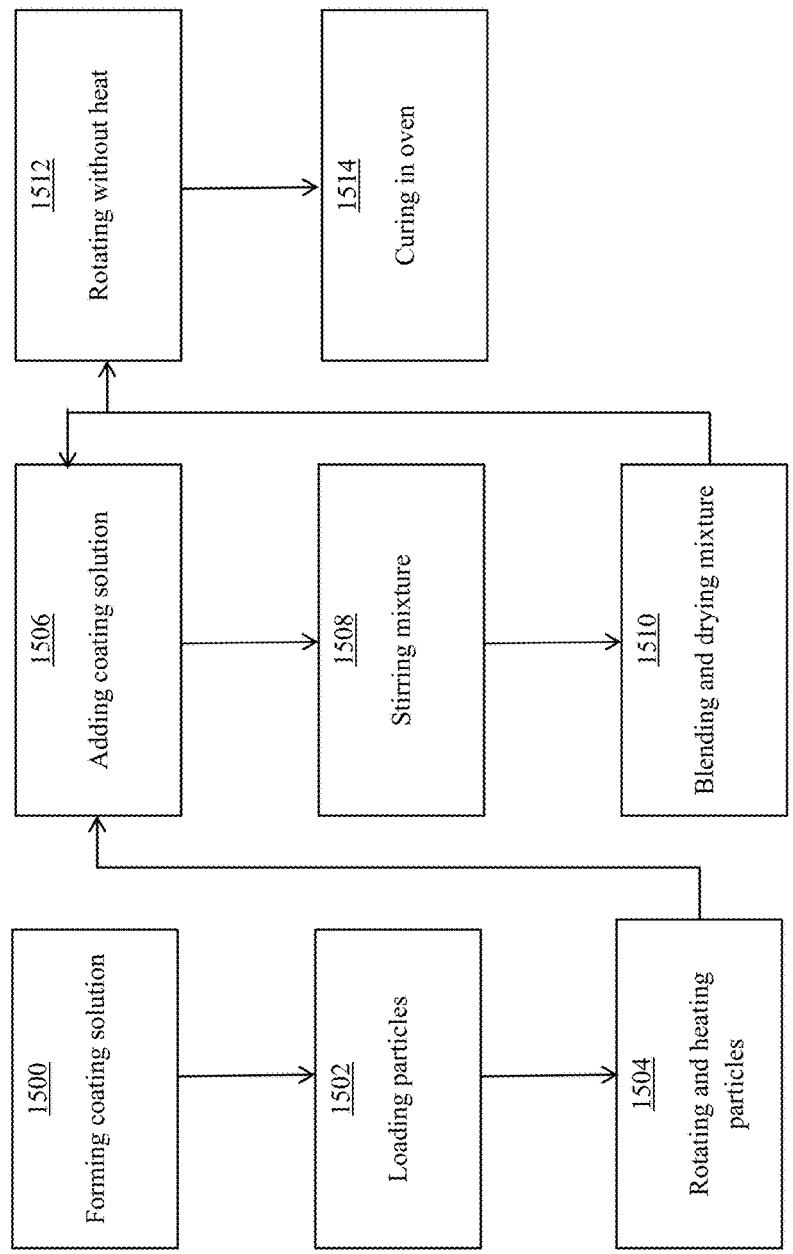
FIG. 15 shows a method of producing acoustic metamaterial particles.

FIG. 15 shows a method of producing acoustic metamaterial particles. The method includes forming a dilute coating solution 1500, loading dense, rigid particles into a pan coating system comprising a rotating drum and heated air blower 1502, rotating the drum and heating the dense, rigid particles with the air blower 1504, adding some of the dilute coating solution to the dense, rigid particles 1506, stirring the mixture of dilute coating solution and dense, rigid particles 1508, blending and drying the mixture in the pan coater until the coating is dry 1510, repeating the process 1506-1510 of adding dilute coating solution, stirring, blending and drying until the dense, rigid particles have an even coating of the dilute coating solution and have approximately doubled in diameter, and leaving the coated particles rotating in the pan coater without heat 1512 and then curing them in an oven 1514.

Figure 16:
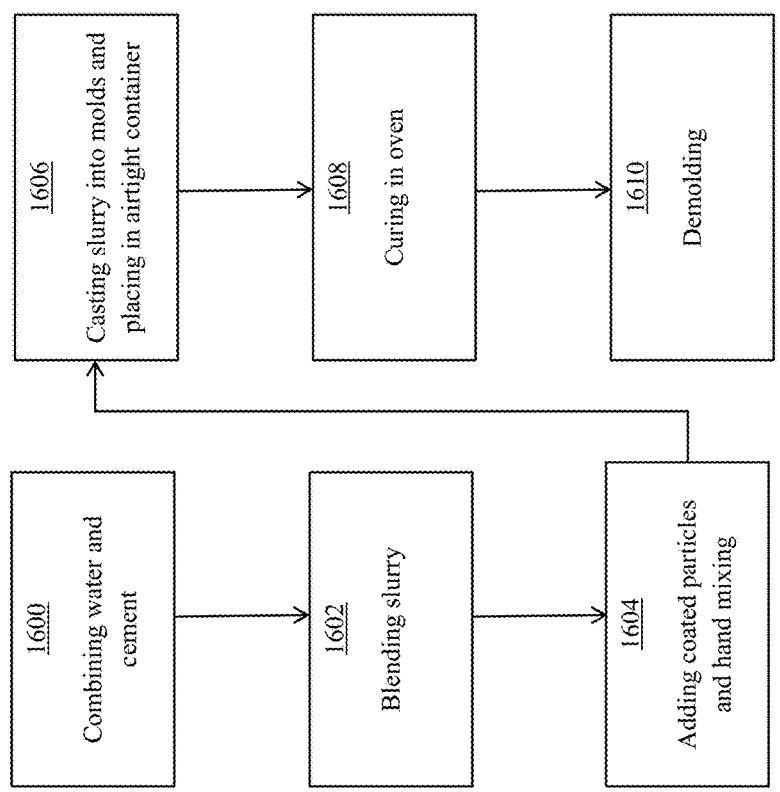
FIG. 16 shows a method of producing a cement composition incorporating acoustic metamaterial particles.

FIG. 16 shows a method of producing a cement composition incorporating acoustic metamaterial particles. The method includes adding Portland cement to water in a running mixer 1600, blending the slurry once the cement has been wetted 1602, adding the coated particles to the slurry and hand mixing 1604, casting the slurry into molds and placing them in an airtight container with moisture-retaining material 1606, placing the airtight container into an oven for curing 1608, and removing the molds from the oven and demolding 1610.

EXAMPLES

Example 1, Silicone Elastomer Coated Steel Balls

A dilute silicone coating solution was formed by adding mineral spirits to clear silicone caulk at a 1:1 ratio and thoroughly mixing. Sixty grams of steel ball bearings of 3/32" diameter were loaded into a pan coating system composed of a rotating drum and heated air blower. The 12" bowl was rotated at approximately 15 RPM and the falling steel balls were heated with the air blower. After several minutes, 50 mL of coating solution were added to the balls. The mixture was stirred with a spatula to ensure even coverage. The contents of the pan coater were left to blend and dry for 20 minutes until the silicone was relatively dry. The coating process was repeated 20 times until the balls had a substantially even coating of silicone as determined by visual inspection. The particles were left in the pan coater rotating overnight without heat and then cured in an oven for two hours at 90° C. The final layered particle size was very uniform with a diameter of 3/16".

Example 2, Cement Composite with Silicone Elastomer Coated Steel Balls

The layered particles of Example 1 were used to create a cement composite. Portland cement was added to deionized water at a ratio of 5:2 in a constant speed mixer running at 4000 RPM. When the cement had been wetted, the slurry was blended at 12,000 RPM for 35 seconds. The layered particles were added to the slurry at 10% by weight of cement and hand mixed. The composite slurry was cast into silicone RTV molds and placed in an airtight container with moist paper towels which was put into a 60° C. oven for curing. After 24 hours, the molds were removed from the oven and container and the samples were demolded. The cement samples were then kept in an airtight container with a water-saturated environment at room temperature.

Example 3, Foam (Low Density) Silicone Coated Tungsten Grit

A foam (low density) silicone coating solution was prepared by adding mineral spirits to silicone caulk at a 2:1 ratio and thoroughly mixing. Glass microballoons of 50 micron average diameter were added at 75% by volume to the silicone solution and folded in until well mixed. The coating mixture was placed in a glass jar for storage until immediate use. 30 mL of tungsten carbide grit approximately 1 mm in length (18 mesh) were added to a 12" pan coating system with heated blower at 25 RPM. After heating the tungsten carbide grit in the rotating system, 10 mL of foam (low density) silicone coating mixture were added. The mixture was stirred with a spatula to ensure even coverage. The contents of the pan coater were left to blend and dry for 8 minutes until the foam (low density) silicone was relatively dry. The coating process was repeated 10 times until the grit had a substantial coating of foam (low density) silicone elastomer as determined by visual inspection. The particles were left in the pan coater rotating overnight without heat. Larger aggregates were removed by sieving and the smaller particles were collected. These were then cured in an oven for two hours at 90° C. The final density of the fine particles was 2.1 g/cc.

Example 4, Cement Composite with Foam (Low Density) Silicone Coated Tungsten Grit The layered particles of Example 3 were used to create a cement composite. Portland cement was added to deionized water at a ratio of 3:1 in a constant speed mixer running at 4000 RPM. When the cement had been wetted, the slurry was blended at 12,000 RPM for 35 seconds. The foamed elastomer layered grit particles were added to the slurry at 20% by weight of cement and hand mixed. The composite slurry was cast into silicone molds and placed in an airtight container with moist paper towels which was put into a 60° C. oven for curing. After 24 hours, the molds were removed from the oven and container and the samples were demolded. The cement samples were then kept in an airtight container with a water-saturated environment at room temperature.

In other embodiments, the various parameters of the described examples may be varied substantially while still producing functional particles. For example, the bowl may be rotated at any of various speeds such as 1-60 RPM, blending and drying may take 5 minutes or more, the coating process may be repeated between 5 and 40 times, the particles may be cured at 60-100° C. for 1-24 hours. The particles (e.g. grit, steel balls) may be heated and combined with the coating solution in various known ways other than a pan coating system, the mixture may be stirred in any known way.

The ratio of cement to water may vary from 1:1 to 6:1, the constant speed mixer may run between 2,000 and 6,000 RPM, the slurry may be blended at 6,000 to 18,000 RPM for 15-60 seconds, the cast slurry may be cured at 50° C. to 90° C. for 12-36 hours. Various moisture-retaining materials may be used in the molds and various methods and tools/machines may be used for mixing.

These and other objectives and features of the invention are apparent in the disclosure, which includes the above and ongoing written specification.

The invention is not limited to the particular embodiments described above in detail. Those skilled in the art will recognize that other arrangements could be devised. In some embodiments, the acoustic metamaterials described herein may be used in formulations other than cement formulations, for example in various other polymers, for which acoustic interrogation may be useful for material characterization and monitoring. The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application. While the invention has been described with reference to specific illustrative embodiments, modifications and variations of the invention may be constructed without departing from the scope of the invention as set forth in the following claims.

We claim:

1. A cement formulation, comprising a base cement slurry and an admixture of acoustic metamaterial particles engineered to influence sound transmission at specific frequencies and act as band gap filters so as to exhibit relative acoustic transparency at most frequencies but reflect much or all sound at particular frequencies, the acoustic metamaterial particles each comprising a dense inner core and a compliant surrounding matrix, wherein the cement formulation exhibits a substantial increase in acoustic transmission loss over the base cement slurry at a first frequency of sound, and does not exhibit a substantial increase in transmission loss over the base cement slurry at a second frequency of sound.

2. The cement formulation of claim 1, wherein the substantial increase in transmission loss is at least 5 dB.

3. The cement formulation of claim 2, wherein the substantial increase in transmission loss is at least 10 dB.

4. The cement formulation of claim 1, wherein the second frequency is within 5 kHz of at least one of the first frequency.

5. The cement formulation of claim 1, wherein at least some of the acoustic metamaterial particles further comprise rigid outer shells.

6. The cement formulation of claim 5, wherein the rigid outer shells comprise epoxy or metal.

7. The cement formulation of claim 1, wherein at least some of the acoustic metamaterial particles further comprise outer coatings and/or surface modifications improving cement matrix bonding.

8. The cement formulation for claim 1, wherein the inner core has a higher density than the compliant surrounding matrix, and wherein the acoustic metamaterial particles have an overall density that matches that of the cement slurry.

9. The cement formulation for claim 1, wherein the dense core comprises at least one of steel, lead, and tungsten.

10. The cement formulation of claim 1, wherein the compliant surrounding matrix comprises at least one of silicone and polyurethane.

11. The cement formulation of claim 1, wherein the metamaterial particles have a diameter between about 50 micrometers to about 2 cm.

12. The cement formulation of claim 1, wherein the cement formulation comprises 0.1-40% of the metamaterial particles by weight.

13. The cement formulation of claim 1, wherein the metamaterial particles are produced using pan coating or a fluidized bed, or by mixing a dense core material and a compliant surrounding matrix material together and pelletizing the mixture.

14. The cement formulation of claim 13, wherein the metamaterial particles are produced by mixing the dense core material and the compliant surrounding matrix material together and pelletizing the mixture, wherein the mixing occurs before the compliant surrounding matrix material has substantially set.

15. The cement formulation of claim 1, wherein the dense inner core is at least partially suspended by the compliant surrounding matrix.

16. A cement interrogation technique, comprising:
transmitting acoustic energy at and near a local resonance frequency of an acoustic metamaterial in an area where a cement formulation comprising the acoustic metamaterial was meant to be placed, the cement formulation comprising a base cement slurry and an admixture of acoustic metamaterial particles engineered to influence sound transmission at specific frequencies and act as band gap filters so as to exhibit relative acoustic transparency at most frequencies but reflect much or all sound at particular frequencies, the acoustic metamaterial particles each comprising a dense inner core and a compliant surrounding matrix, wherein the cement formulation exhibits a substantial increase in acoustic transmission loss over the base cement slurry at a first frequency of sound, and does not exhibit a substantial increase in transmission loss over the base cement slurry at a second frequency of sound;
detecting an acoustic response;
analyzing the acoustic response for band-gap performance comprising substantially elevated transmission loss at or near a given first frequency that rapidly falls off to non-elevated levels of transmission loss at nearby frequencies;
determining that the cement formulation is present in regions exhibiting band-gap performance; and
determining that the cement formulation is not present and/or has been compromised in regions not exhibiting band-gap performance.

17. The method of claim 16, further comprising determining a band gap frequency and/or a response shape of an interrogated material based on the acoustic response, determining a difference between the determined band gap frequency of the interrogated material and the local resonance frequency of the acoustic metamaterial, and using the difference and/or the response shape to determine stress and/or curing progression in the interrogated material.

18. The method of claim 17, further comprising determining that the local resonance frequency is greater than the band-gap frequency of the acoustic metamaterial, and determining that the interrogated material is under high stress.

19. The cement formulation of claim 1, wherein the dense inner cores of the acoustic metamaterial particles have a density of 3 to 15 g/cc and a Young's modulus of greater than 5 GPa and the compliant surrounding matrix of each acoustic metamaterial particle is less dense and more compliant than the corresponding dense inner core and has a Young's modulus of less than 10 GPa.

20. The cement formulation of claim 1, wherein an overall density of the acoustic metamaterial particles is between 1.9 g/cc and 3.2 g/cc.

* * * * *